United States Patent [19]

Brown

[11] Patent Number: 5,157,150
[45] Date of Patent: Oct. 20, 1992

[54] PREPARATION OF 2-(CHLORO, BROMO OR NITRO)-4-(ALKYLSULFONYL)BENZOIC ACIDS AND INTERMEDIATES

[75] Inventor: Richard W. Brown, Richmond, Calif.

[73] Assignee: Imperial Chemical Industries PLC, London, United Kingdom

[21] Appl. No.: 641,242

[22] Filed: Jan. 15, 1991

Related U.S. Application Data

[62] Division of Ser. No. 470,009, Jan. 25, 1990, Pat. No. 5,008,448, which is a division of Ser. No. 280,787, Dec. 7, 1988, abandoned.

[51] Int. Cl.$^5$ .................... C07C 61/00; C07C 315/00
[52] U.S. Cl. ........................................ 562/125; 568/31
[58] Field of Search ........................................ 562/125

[56] References Cited

U.S. PATENT DOCUMENTS 4,211,723  7/1980  Koike et al. .................... 562/833

OTHER PUBLICATIONS

Taylor et al, "Kinetics of Complex Formation between Human Carbonic Anhydrases and Aromatic Sulfonamides", *Biochemistry* vol. 9 No. 13 pp. 638–645.
Cain, et al. "Potential Antitumor Agents" *Joun. of Med. Chem.* vol. 12/9 pp. 922–930.

*Primary Examiner*—Jose G. Dees
*Assistant Examiner*—Keith MacMillan
*Attorney, Agent, or Firm*—Edwin H. Baker; Michael J. Bradley

[57] ABSTRACT

A process for the preparation of 2-(chloro, bromo or nitro)-4-(alkylsulfonyl)benzoic acid and to intermediates used in the process.

4 Claims, No Drawings

PREPARATION OF 2-(CHLORO, BROMO OR NITRO)-4-(ALKYLSULFONYL)BENZOIC ACIDS AND INTERMEDIATES

This is a divisional of application Ser. No. 07/470,009 filed Jan. 25, 1990, now U.S. Pat. No. 5,008,448 which is a divisional of application Ser. No. 07/280,787, filed Dec. 7, 1988, abandoned.

BACKGROUND OF THE INVENTION

This invention relates to a process for the preparation of 2-(chloro, bromo or nitro)-4-(alkylsulfonyl)benzoic acids and to intermediates useful in the process.

These 2-(chloro, bromo or nitro)-4-(alkylsulfonyl)-benzoic acids are intermediates useful for the preparation of certain 2-(2-chloro, bromo or nitro)-4-(alkylsulfonyl)benzoyl-1,3-cyclohexanedione herbicides. The 2-(chloro, bromo or nitro)-4-(alkylsulfonyl)benzoic acid is converted to its acid chloride or cyanide and it is reacted with certain 1,3-cyclohexanediones according to the process of U.S. Pat. No. 4,695,673 or U.S. Pat. No. 4,708,127.

SUMMARY OF THE INVENTION

One embodiment of this invention is directed to a process for the preparation of 2-(chloro, bromo or nitro)-4-(alkylsulfonyl)benzoic acids, represented by the following reaction steps:

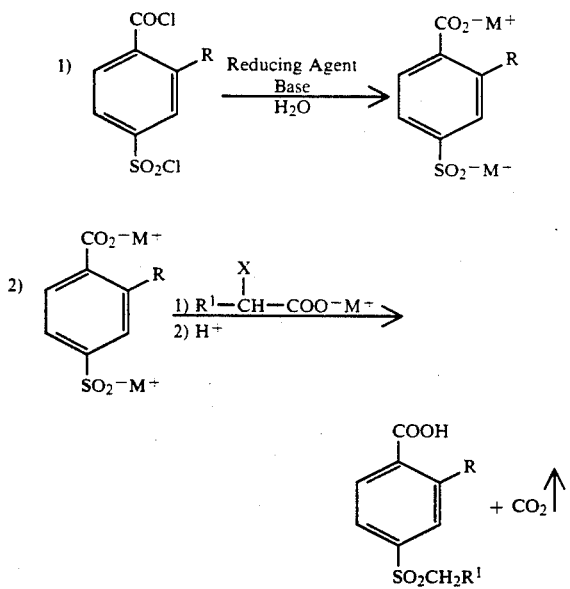

The 2-(chloro, bromo or nitro)-4-(chlorosulfonyl)-benzoyl chloride [reactant of Step (1)] can be prepared by the following reaction:

In the above Reaction Steps (1), (2) and (3), R is chloro, bromo or nitro; $R^1$ is hydrogen or $C_1$-$C_3$ alkyl, preferably methyl or ethyl, most preferably $R^1$ is hydrogen; M is hydrogen, sodium, potassium or ammonium, preferably sodium; and X is chloro, bromo or iodo, preferably chloro.

A second embodiment of this invention is the intermediate reaction product of Reaction Step (3). This 2-(chloro, bromo or nitro)-4-(chlorosulfonyl)benzoyl chloride intermediate has the structural formula

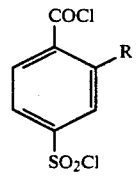

wherein R is chloro, bromo or nitro.

A third embodiment of this invention is the intermediate reaction product of Reaction Step (1). This second intermediate has the structural formula

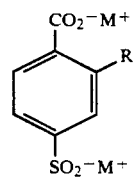

wherein R is chloro, bromo or nitro and M is hydrogen, sodium, potassium or ammonium.

DETAILED DESCRIPTION OF THE INVENTION

Referring to the three reaction steps under the "Summary of the Invention" section, the following is additionally taught.

The process of this invention is depicted by Reaction Steps (1) and (2). Step (3) is provided to show a process for the preparation of the intermediate 2-(chloro, bromo or nitro)-4-(chlorosulfonyl)benzoyl chloride which is an embodiment of this invention. Also the intermediate reaction product of Reaction Step (1) is an embodiment of the invention.

Generally in Reaction Step (1) the 2-(chloro, bromo or nitro)-4-(chlorosulfonyl)benzoyl chloride reaction product of Reaction Step (3) preferably is reacted with an equimolar amount of a reducing agent, preferably sodium or potassium sulfite, along with a base, preferably an inorganic base, having a sodium, potassium or ammonium cation. Such bases are sodium or potassium hydroxide, sodium or potassium bicarbonate or ammonium hydroxide. Preferably the base is sodium bicarbonate. Generally about 3 or more moles of the base are used, preferably between about 4.0 to 4.5 moles. The reaction preferably should be run at a pH of about 7-9. The reaction is run in water, optionally in the presence of a non-miscible organic solvent. During Reaction Step (1), the sulfonyl chloride group is reduced to the sodium, potassium or ammonium salt of the corresponding sulfinate and the acid chloride group is hydrolyzed to the sodium, potassium or ammonium salt of the benzoic acid. Reaction Step (1) is preferably run at a temperature above about 0° C., more preferably between about 20° C. to about 100° C., even more preferably between about 30° C. to about 75° C. and most preferably between about 40° C. and about 50° C. When "R" is nitro, the reaction preferably should be run at a temperature between about 10° C. to about 20° C. The reaction at the most preferable temperature or above is very quick and normally takes less than 15 minutes.

The reaction product is soluble in the aqueous solvent and normally is not isolated.

Reaction Step (2) is carried out by adding a mole of the sodium, potassium or ammonium salt of an α-halocarboxylic acid of the structural formula

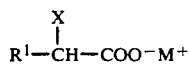

wherein $R^1$ is hydrogen, $C_1$-$C_3$ alkyl, preferably methyl, ethyl or n-propyl, more preferably hydrogen; M is sodium, potassium or ammonium; and X is chloro, bromo or iodo, preferably chloro, to the aqueous reaction product of Reaction Step (1). In the alternative, the above salt of an α-halocarboxylic acid can be formed in situ by adding equal molar amounts of an α-halocarboxylic acid of the structural formula

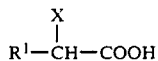

where $R^1$ and X are as defined with an inorganic base having a sodium, potassium or ammonium cation. Such bases are the same as defined in Reaction Step (1). The reaction is carried to completion by heating the reaction mixture to reflux for about 6–48 hours. The reaction time can be reduced by heating the reaction mixture at higher temperatures under pressure.

Generally in Reaction Step (3), the reaction between the benzoic acid reactant and the thionyl chloride is run in conventional equipment using excess thionyl chloride and at least 5 mole percent of the dimethylformamide (DMF) catalyst. Preferably, the reaction is run in an inert solvent such as toluene or ethylene dichloride, or excess thionyl chloride can serve as the solvent. Preferably, the reaction is run at a temperature between about 50° C. to about 100° C. in the absence of moisture. The reaction product is recovered by conventional techniques such as separating solids by filtration and evaporating excess solvent from the filtrate to yield the desired reaction product.

As previously recited, an embodiment of this invention is directed to a process for preparing 2,4-disubstituted benzoic acid compounds having the structural formula

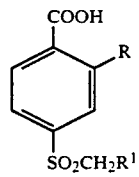

wherein R is chloro, bromo or nitro and $R^1$ is hydrogen or $C_1$-$C_3$ alkyl, by 1) reacting a compound having the structural formula

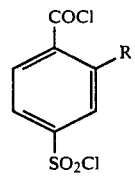

wherein R is as defined with a reducing agent along with a base, preferably an inorganic base, having a sodium, potassium or ammonium cation in an aqueous medium to prepare an intermediate having the structural formula

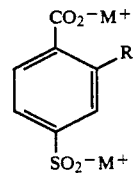

wherein R is chloro, bromo or nitro and M is hydrogen, sodium, potassium or ammonium, followed by 2) reacting the intermediate from step (1) with a salt having the structural formula

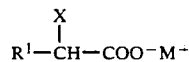

wherein X is chloro, bromo or iodo; $R^1$ is hydrogen or $C_1$-$C_3$ alkyl and M is sodium, potassium or ammonium, to prepare a salt of a benzoic acid having the structural formula

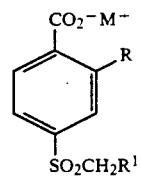

wherein M, R and $R^1$ are as defined and finally acidifying the salt to prepare the desired product having the structural formula

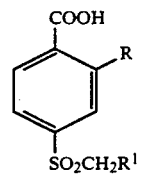

wherein R and $R^1$ are as defined.

The intermediate benzoic acids of Reaction Step (2) can easily be converted to their respective acid chlorides and then to their acid cyanides, if desired, by the following two reactions. First, a mole of oxalyl chloride and a catalytic amount of dimethylformamide in a suitable solvent such as methylene chloride is heated at a temperature of 20° to 40° C. for 1 to 4 hours with a mole of the intermediate benzoic acid. The corresponding benzoic acid cyanide can easily be prepared from the benzoic acid chloride by reaction with cuprous cyanide at a temperature of 50° to 220° C. for 1 to 2 hours.

The following series of examples teach the synthesis of representative intermediate compounds of this invention and the processes of this invention. The structures of all compounds of the examples and tables were verified by nuclear magnetic resonance (NMR), infrared spectroscopy (IR) and mass spectroscopy (MS).

EXAMPLE 1

2-Chloro-4-(chlorosulfonyl)benzoyl Chloride

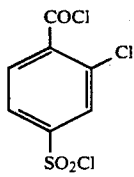

A 25 milliliter (mL) round bottom flask equipped with reflux condenser, thermometer, and magnetic stirrer was charged with 3.2 grams (g) [10.0 millimole (mmol)] of the potassium salt of 2-chloro-4-sulfobenzoic acid (85 wt. % pure), 10 mL (140 mmol) of thionyl chloride and 0.03 g (0.5 mmol) of dimethylformamide (DMF). After heating for one hour at 60° C., the cooled reaction mixture was diluted with 10 mL of toluene, filtered and evaporated to afford 2.55 g (100% yield) of 2-chloro-4-(chlorosulfonyl)benzoyl chloride as a brown oil.

EXAMPLE 2

2-Chloro-4-(methylsulfonyl)benzoic Acid Using Chloroacetic Acid and Sodium Hydroxide

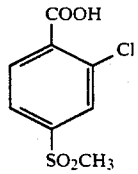

A 250 mL round bottom flask equipped with a reflux condenser, thermometer, and magnetic stirrer was charged with 9.2 g (73 mmol) of sodium sulfite, 24.6 g (292 mmol) of sodium bicarbonate and 80 mL of water. The resulting slurry was heated to 50° C., and 20.0 g (70 mmol) of 2-chloro-4-(chlorosulfonyl)benzoic acid was added over 15 minutes. After heating at 50° C. for three hours, chloroacetic acid (10.4 g, 110 mmol) and 5.7 mL (110 mmol) of 50% aqueous sodium hydroxide were added sequentially to the aqueous solution of 2-chloro-4-sulfinylbenzoic acid, and the reaction mixture heated to reflux. After heating for 19 hours, the reaction mixture was allowed to cool to ambient temperature and acidified with dilute HCl. The precipitated solids were collected by filtration, washed with dilute HCl and dried to give 17.4 g of 2-chloro-4-(methylsulfonyl)benzoic acid as a white solid. The solid was assayed at 85% purity, corresponding to an overall yield of 89%.

EXAMPLE 3

2-Chloro-4-(methylsulfonyl)benzoic Acid Using the Sodium Salt of Chloroacetic Acid

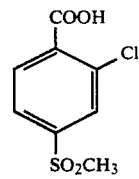

A 100 mL round bottom flask equipped with a reflux condenser, thermometer, and magnetic stirrer was charged with 4.6 g (37 mmol) of sodium sulfite, 12.3 g (146 mmol) of sodium bicarbonate and 40 mL of water. The resulting slurry was heated to 75° C. and 10 g (33 mmol) of 2-chloro-4-(chlorosulfonyl)benzoyl chloride was added slowly. After stirring at 75° C. for 2 hours, 6.4 g (55 mmol) of the sodium salt of chloroacetic acid was added and the reaction mixture heated at reflux for 21 hours. The cooled reaction mixture was acidified with dilute HCl and extracted with ethyl acetate. The organic layer was dried with magnesium sulfate and evaporated to dryness to afford 7.5 g of 2-chloro-4-(methylsulfonyl)benzoic acid as a white solid. This material was shown to be 87% pure, representing an 85% overall yield.

EXAMPLE 4

2-Bromo-4-(chlorosulfonyl)benzoyl chloride

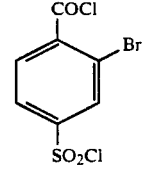

A 100 mL round bottom flask equipped with reflux condenser, temperature controller and magnetic stirrer was charged with 8.8 g (28 mmol) of the potassium salt of 2-bromo-4-sulfobenzoic acid, 21.5 mL (301 mmol) of thionyl chloride, and 0.12 g (1.7 mmol) of DMF. After heating for five hours, the cooled reaction mixture was filtered and evaporated to afford the desired product, 2-bromo-4-(chlorosulfonyl)benzoyl chloride.

EXAMPLE 5

2-Bromo-4-(methylsulfonyl)benzoic Acid

A 50 mL round bottom flask equipped with a reflux condenser, thermometer and magnetic stirrer was charged with 1.6 g (13 mmol) of sodium sulfite, 4.2 g (50 mmol) of sodium bicarbonate and 20 mL of water. The resulting slurry was heated to 75° C. and 4.0 g (13 mmol) of 2-bromo-4-(chlorosulfonyl)benzoyl chloride was added over 30 minutes. After heating at 75° C. for one hour, chloroacetic acid (1.8 g, 19 mmol) and 1.0 mL (19 mmol) of 50% aqueous sodium hydroxide were added sequentially to the aqueous solution of 2-bromo-4-sulfinylbenzoic acid, and the reaction mixture heated to reflux. Additional chloroacetic acid (2.0 g) was added as necessary to drive the reaction to completion. After heating for 16 hours, the reaction mixture was allowed to cool to ambient temperature and acidified with concentrated HCl. The precipitated solids were collected by filtration and dried to give 1.6 g of 2-bromo-4-(methylsulfonyl)benzoic acid, corresponding to a 46% yield.

EXAMPLE 6

2-Nitro-4-(chlorosulfonyl)benzoyl Chloride

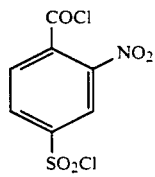

A 250 mL round bottom flask equipped with reflux condenser, thermometer, and magnetic stirrer was charged with 9.0 g (32 mmol) of the potassium salt of 2-nitro-4-sulfobenzoic acid, 10.7 mL (142 mmol) of thionyl chloride, 0.23 g (3.2 mmol) of DMF and 40 mL of toluene. After heating for one hour at 85° C., the cooled reaction mixture was filtered and evaporated to afford 8.2 g (92% yield) of 2-nitro-4-(chlorosulfonyl)-benzoyl chloride as an amber oil.

EXAMPLE 7

2-Nitro-4-(methylsulfonyl)benzoic Acid

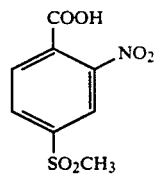

A 100 mL round bottom flask equipped with a reflux condenser, thermometer and magnetic stirrer was charged with 1.9 g (15 mmol) of sodium sulfite, 5.1 g (60 mmol) of sodium bicarbonate and 20 mL of water. The resulting slurry was cooled to 15° C. and 4.0 g (14 mmol) of 2-nitro-4-(chlorosulfonyl)benzoyl chloride was added over 5 minutes. The reaction mixture was stirred at 15° C. for three hours and then at ambient temperature overnight. After warming to 40° C., 3.1 g (27 mmol) of the sodium salt of chloroacetic acid was added to the aqueous solution of 2-nitro-4-sulfinylbenzoic acid and the reaction mixture heated to reflux. After heating for 7 hours, the reaction mixture was allowed to cool to ambient temperature, diluted with 30 mL of water and washed with 50 mL of ethyl acetate. The aqueous layer was acidified with concentrated HCl and extracted with 75 mL of ethyl acetate. The organic solution was concentrated to afford 3.0 g (87% yield) of 2-nitro-4-(methylsulfonyl)benzoic acid as a pale yellow solid.

What is claimed is:

1. An intermediate compound having the structural formula

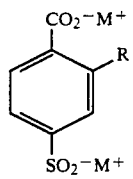

wherein R is chloro, bromo or nitro and M is hydrogen, sodium, potassium or ammonium.

2. The compound of claim 1 wherein R is chloro and M is sodium.

3. The compound of claim 1, wherein R is bromo and M is sodium.

4. The compound of claim 1, wherein R is nitro and M is sodium.